(12) United States Patent
Nasarabadi et al.

(10) Patent No.: US 7,083,951 B2
(45) Date of Patent: Aug. 1, 2006

(54) FLOW CYTOMETRIC DETECTION METHOD FOR DNA SAMPLES

(75) Inventors: Shanavaz Nasarabadi, Livermore, CA (US); Richard G. Langlois, Livermore, CA (US); Kodumudi S. Venkateswaran, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 14 days.

(21) Appl. No.: 10/077,321

(22) Filed: Feb. 14, 2002

(65) Prior Publication Data

US 2002/0155482 A1 Oct. 24, 2002

Related U.S. Application Data

(60) Provisional application No. 60/268,852, filed on Feb. 14, 2001.

(51) Int. Cl.
C12Q 1/68 (2006.01)
C12P 19/34 (2006.01)
C07H 21/04 (2006.01)

(52) U.S. Cl. ............ 435/91.2; 435/6; 435/287.2; 536/24.3; 536/24.33

(58) Field of Classification Search ............ 435/6, 435/91.2, 320.1, 91.1, 183, 287.2; 530/350, 530/367; 436/94, 800, 805; 536/23.4, 23.1, 536/24.3, 24.33; 548/111, 304.1
See application file for complete search history.

(56) References Cited

U.S. PATENT DOCUMENTS 5,552,540 A * 9/1996 Haralambidis ............ 536/25.34
5,981,180 A * 11/1999 Chandler et al. ............... 435/6
5,989,813 A 11/1999 Gerdes
6,221,600 B1 * 4/2001 MacLeod ........................ 435/6
6,287,766 B1 * 9/2001 Nolan et al. ..................... 435/6
6,649,414 B1 * 11/2003 Chandler et al. ............. 436/63

FOREIGN PATENT DOCUMENTS

WO  WO 99/58955 A1  12/1999
WO  WO 00/68434 A2  12/2000
WO  WO 01/13120 A1  2/2001

OTHER PUBLICATIONS

Armstrong et al., "Suspension Arrays for High Throughput, Multiplexed Single Nucleotide Polymorphism Genotyping," Cytometry, vol. 40, 2000, pp. 102-108.*
M.P. Weiner et al Flow Cytometric Platform for High-throughput Single Nucleotide Polymorphism Analysis Biotechniques 30 661-669 Mar. 2000.

(Continued)

Primary Examiner—Bradley L. Sisson
(74) Attorney, Agent, or Firm—John H. Lee; Alan H. Thompson; Ann M. Lee (57) ABSTRACT

Disclosed herein are two methods for rapid multiplex analysis to determine the presence and identity of target DNA sequences within a DNA sample. Both methods use reporting DNA sequences, e.g., modified conventional Taqman® probes, to combine multiplex PCR amplification with microsphere-based hybridization using flow cytometry means of detection. Real-time PCR detection can also be incorporated. The first method uses a cyanine dye, such as, Cy3™, as the reporter linked to the 5' end of a reporting DNA sequence. The second method positions a reporter dye, e.g., FAM, on the 3' end of the reporting DNA sequence and a quencher dye, e.g., TAMRA, on the 5' end.

30 Claims, 4 Drawing Sheets

FAM

OTHER PUBLICATIONS

Jingwen Chen et al Fluorescent Microsphere Biased Readout Technology for Multiplexed Human Single Nucleotide Polymorphism Analysis and Bacterial Identification Human Mutatioins 17: 305-316 (2001).

M.P. Weiner et al Multiplexed Single Mucleotide Polymorphism Genotyping by Oligonucleotide Ligation and Flow Cytometry Cytometry 39: 131-140 (2000).

J R. Kettman Jr. et al Advanced Multiplex Analysis with the Flow Metrix System Clinical Chemistry 43: 1749-1756 (1997).

J.A. Steinkamp et al Flow Cytometry-Based Minisequencing: A New Platform for High Throughput single-Nucleotide Polymorphism Scoring Genomics 66 135-143 (2000).

A. Muzumder et al Suspension Arrays for High Throughput, Multiplexed Single Mucleotide Polymorphism Genotyping Cytometry 40:102-108 (2000).

R.J. Fulton t al Classification and Properties of 64 Multiplexed Microshpere Sets Cytometry 33; 234-243 (1998).

Brown et al A Bead-Based Method for Multiplexed Identification and Quantitation of DNA Sequences Using Flow Cytometry Applied and Environmental Microbiology Oct. 2000 pp. 4258-4265.

W.J. Wilson et al "A Multiplexed PCR-coupled liquid bead array for the simultaneous detection of four biothreat agents" , Molecular and Cellular Probes, Apr. 2005;19(2): 137-144.

B.J. Hindson et al "Autonomous Detection of Aerosolized Biological Agents by Multiplexed Immunoassay with Polymerase Chain Reaction Confirmation", Anal Chem, Jan. 2005; 77(1): 284-289.

J.A. Higgins et al "A Handheld Real Time Thermal Cycler for Bacterial Pathogen Detection", Biosens Bioelectron, Aug. 2003; 18(9): 1115-11123.

C.J.Elkin et al "A Reusable Flow-Trough Polymerase Chain Reaction Instrument for the Continuous Monitoring of Infectious Biological Agents" Anal. Chem vol. 75; No. 14 Jul. 15, 2003; 3446-3450.

* cited by examiner

FAM

Figure 1

TAMRA

FLOW CYTOMETRIC DETECTION METHOD FOR DNA SAMPLES

RELATED APPLICATION

This application relates to U.S. Provisional Application No. 60/268,852 filed Feb. 14, 2001, and claims priority under 35 U.S.C. 120.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Bead based hybridization assays have been reported for multiplexed detection of PCR amplified products. Each published method is well suited to a specific application. Published bead based hybridization assays require more than one step for hybridization, are time consuming and are not easily automated.

In a method disclosed by Brown et al, *A Bead-Based Method for Multiplexed Identification and Quantitation of DNA Sequencs Using Flow Cytometry*, Applied and Environmental Microbiology, October: 4258–4265, (2000), a double stranded amplified DNA is enzymatically digested with Shrimp alkaline phosphatase (SAP) and Exonuclease1. The single stranded DNA produced from the digestion is then annealed to an oligonucleotide on a bead and the hybridized product is detected with the Luminex flow analyzer.

Weiner et al, *Multiplexed Single Nucleotide Polymorphism Genotyping by Oligonucleotide Ligation and Flow Cytometry*, Cytometry 39:131–140 (2000), describes a universal ZipCode hybridization method. In this method, a complementary ZipCode sequence is attached to a long piece of DNA that is attached to a spacer used to reduce the stearic hindrance. A part of the allele complementary sequence is attached to the ZipCode sequence. A capture probe is then prepared by hybridization and ligation of the allele complementary sequence and a fluorescently labeled allele complementary sequence in the presence of the single stranded amplified DNA and ligase enzyme.

In *Suspension Arrays for High Throughput, Multiplexed single Nucleotide Polymorphism Genotyping*, Cytometry 40:102–108 (2000), Muzumder et al describes a more simplistic, but difficult approach. Their approach denatures a fluorescently labeled denatured PCR product and directly hybridizes that product to complementary oligonucleotides attached to beads.

Each of the above mentioned assays take on average several hours to go from amplification to detection. Holland et al in, *Detection of specific polymerase chain reaction product by utilizing the 5' - - - 3' exonuclease activity of Thermus aquaticus DNA polymerase*, Proc Natl Acad Sci USA 88 (16):7276–80, (1991), discloses real time PCR amplification. This method is generally referred to as Taqman® real time detection and is routinely used for real-time PCR amplification. Real time PCR amplification is measured using fluorogenic probes that can detect the 5'-exonuclease activity of the DNA polymerase. At present, Taqman® real time detection can simultaneously detect a maximum of four nucleic acid targets.

SUMMARY OF THE INVENTION

Aspects of the invention include a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a fluorophore on the 5' end, forming a background PCR product by conducting the background multiplex PCR amplification reaction, wherein the background PCR amplification reaction is run under the same conditions and using the same primers and reagents as the sample PCR amplification reaction, forming a microsphere mix comprising a plurality of optically encoded microspheres bound to a plurality of oligonucleotides, wherein each optical code corresponds to specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

Another aspect of the invention includes a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a fluorophore on the 5' end and a quencher on the 3' end, forming a background PCR product by conducting the background multiplex PCR amplification reaction, wherein the background PCR amplification reaction is run under the same conditions and using the same primers, reagents and reporting DNA sequences as the sample PCR amplification reaction, determining with on-line fluorescence detecting means whether a difference in fluorescence exists between the sample PCR product and the background PCR product, the difference being indicative of the multiplex PCR amplification reaction resulting in the formation of (1) at least one PCR amplification product and (2) at least one residual reporting sequence containing the quencher, forming a microsphere mix comprising a plurality of optically encoded microspheres bound to a plurality of oligonucleotides, wherein each optical code corresponds to specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

Another aspect of the invention includes a method for multiplexed detection of PCR amplified products comprising: providing at least one DNA sample for a sample multiplex PCR amplification reaction, providing necessary reagents and primers for the sample multiplex PCR amplification reaction and a background multiplex PCR amplification reaction, forming a sample PCR product by conducting the sample multiplex PCR amplification reaction using at least one reporting DNA sequence complementary to a region on at least one target DNA sequence, wherein the reporting DNA sequence has a quencher on the 5' end and a fluorophore on the 3' end, forming a background PCR product by conducting the background multiplex PCR amplification reaction, wherein the background PCR amplification reaction is run under the same conditions and using the same primers, reagents and reporting DNA sequences as the sample PCR amplification reaction, determining with on-line fluorescence detecting means whether a difference in fluorescence exists between the sample PCR product and the background PCR product, the difference being indicative of the multiplex PCR amplification reaction resulting in the formation of (1) at least one PCR amplification product and (2) at least one residual reporting sequence containing the fluorophore, forming a microsphere mix comprising a plurality of optically encoded microspheres bound to a plurality of oligonucleotides, wherein each optical code corresponds to specific oligonucleotide having a DNA sequence complementary to at least one reporting DNA sequence, forming a sample hybridization product by adding the sample PCR product to the microsphere mix, forming a background hybridization product by adding the background PCR product to the microsphere mix, determining the existence of the target DNA sequence specified by the reporting DNA sequence by comparing the fluorescence of the sample hybridization product with the background hybridization product using flow cytometry.

DETAILED DESCRIPTION

Disclosed herein is a simple and rapid method for the multiplexed detection of PCR amplified product by fluorescent microsphere, i.e., bead, flow analysis. Multiplexed detection of PCR amplified products is possible using a fluorescent reporter and a microsphere-based hybridization. A dual detection system is disclosed wherein the presence of target DNA sequences can be identified. A reporting DNA sequence, such as, Taqman.RTM., real time PCR detection is used in conjunction with microsphere array based multiplexed hybridization identification. First, a real time PCR detection means, such as an Applied Biosystems ABI 7700 instrument, is used to detect whether any PCR amplification products were formed during the PCR amplification process. The instrument disclosed in U.S. Provisional Patent Application 60/303,637 filed on Jul. 6, 2001, by Colston et al, assigned to the same assignee, can also be used to detect the presence of PCR amplification products.

A secondary confirmation of the amplification is then accomplished by hybridization of the cleaved DNA reporting sequence fragments resulting from the amplification process and unused reporting sequences to a plurality of fluorescently-labeled microspheres linked to probes complementary to the DNA reporting sequences. The hybrids are then detected using flow cytometry means. Avidin-coated and Carboxylated polystyrene fluorescently-labeled microspheres are effective, such as, Fluorescent microspheres from Luminex Corporation of Austin, Tex. However, fluorescently-labeled microspheres made of other materials and from other manufacturers can also be used. Changes in fluorescence intensity of any hybrid indicates the existence of the target sequence corresponding to the specific probe.

Figure 1:
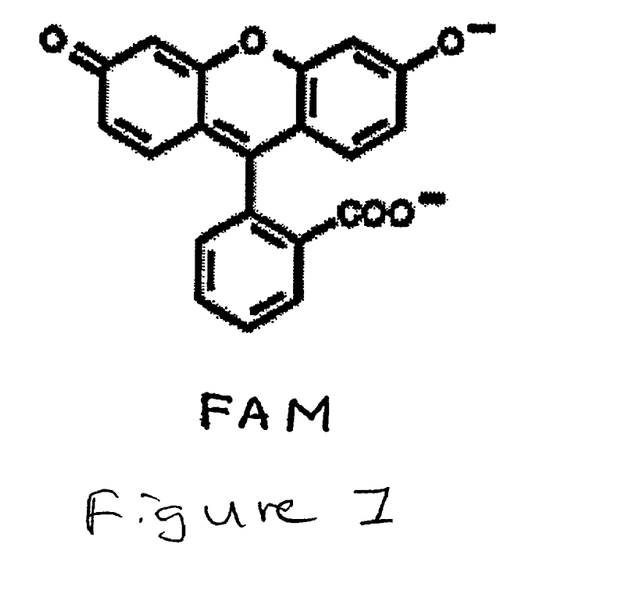
FIG. 1 shows the chemical structure of FAM.
Figure 2:
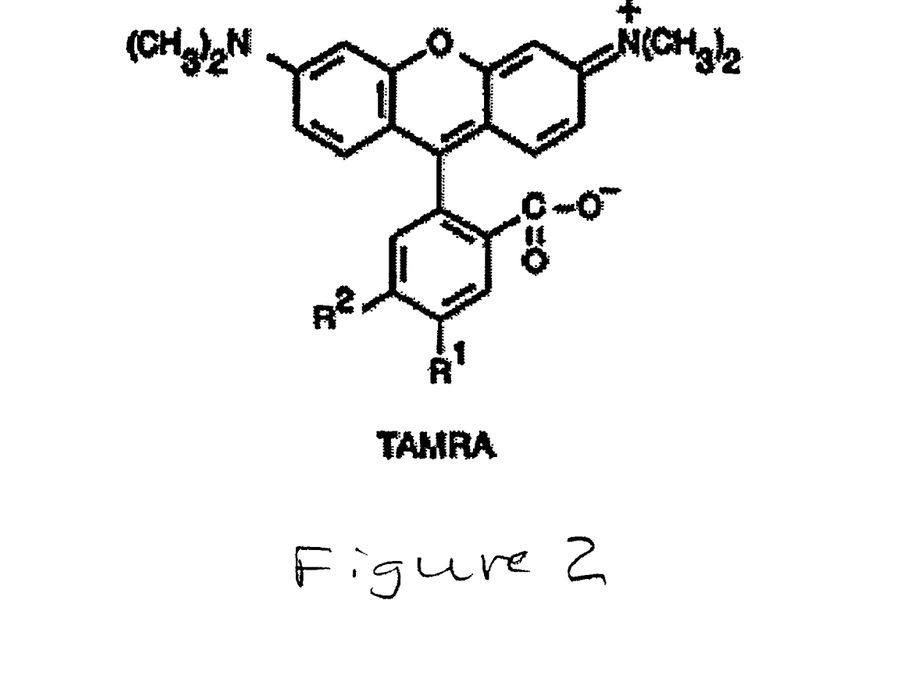
FIG. 2 shows the chemical structure of TAMRA.

Conventional Taqman® real time PCR reactions take advantage of the 5' to 3' exonuclease activity of the enzyme Taq Polymerase and fluorescence resonance energy transfer (FRET) in order to detect real time PCR amplification of DNA. The Taqman® reaction mixture contains a labeled reporting DNA sequence, e.g., a Taqman® probe, typically 20 to 24 bases long with a fluorophore, i.e., fluorescent reporter dye, on the 5' end and a quencher, i.e., quencher dye, on the 3' end. The reporting DNA sequence, e.g., a Taqman® probe, is complementary to a target DNA sequence. For example in the TAM-FAM labeled reporting sequence, the fluorescent reporter dye, 6-carboxyfluorescein (FAM), is covalently linked to the 5' end of the oligonucleotide and the quencher dye, 6-carboxy-N,N,N',N'-tetramethylrhodamine (TAMRA) is linked to the 3' end. FIG. 1 shows the chemical structure of FAM and FIG. 2 shows the chemical structure of TAMRA. During the amplification reaction, the 5' to 3' exonuclease activity of the Taq polymerase cleaves the reporting DNA sequence between the fluorophore and the quencher only if the reporting DNA sequence hybridizes to the target. The reporting DNA sequence fragments are then displaced from the target, and polymerization of the strand continues. The 3' end of the reporting DNA sequence is blocked to prevent extension of the reporting DNA sequence during PCR. The result is that the fluorophore is no longer in close proximity of the quencher and the instrument is able to detect the fluorescent wavelength of the fluorophore. The fluorescence can be measured, and it is in direct proportion to the amount of target DNA being produced. Thus, accumulation of PCR products is detected directly by monitoring the increase in fluorescence of the fluorophore. The increase is determined by comparing the sample signal to a background signal, i.e., a real time PCR reaction without the addition of any target DNA sequence.

The number of fluorophore-quencher pairs available for use during an analysis is limited by their excitation-emission wavelength and whether that wavelength is within the detection parameters of the instrument used. As new dyes are developed, the spectral range of detection continues to expand. The principles involved in the conventional Taqman.RTM. 5' exonuclease assay are described in more detail by Holland et al in, Detection of specific polymerase chain reaction product by utilizing the 5'–3' exonuclease activity of Thermus aquaticus DNA polymerase, Proc Natl Acad Sci USA 88 (16):7276–80, 1991. A few examples of typical PCR instruments include the ABI prism 7700, the Cepheid Smart Cycler, and the Bio-Rad iCycler.

Typically, the PCR reaction mixture comprises 1×PCR buffer, 6 mM of 4.5 M $MgCl_2$, dNTPs (about 2.5 mM each, except about 5 mM for UTP), about 1.25 U of Pt Taq polymerase(GibcoBRL), 400 nM of each primer and 400 nM of each reporting DNA sequence, about 5 μL of sample and PCR water such that the total volume of the mixture is about 25 µL. The enzyme Uracil N-glycosylase (UNG) may be used for decontamination. If UNG is used in the reaction, then about 1U of UNG is used per 50 µL of PCR reaction mixture and an initial cycle of about 50° C. for about 2 minutes is performed. The PCR commences with an initial single cycle of (96° C. for 1 minute). The PCR thermal cycling parameters are dependent on the melting temperatures (Tm's) of the primers, but typically are around 45 cycles of (96° C. for 10 seconds, 60° C. for 60 seconds).

If the instrument disclosed in U.S. Provisional Patent Application 60/303,637 filed on Jul. 6, 2001, by Colston et al, assigned to the same assignee, is used, then the thermal cycling conditions are one cycle (92.degree. C. for 10 seconds), followed by 40 cycles of (94.degree. C., 5 seconds: 57.degree. C., 15 seconds). The total reaction time is about 10–15 minutes depending on the length of the cycling.

Figure 3:
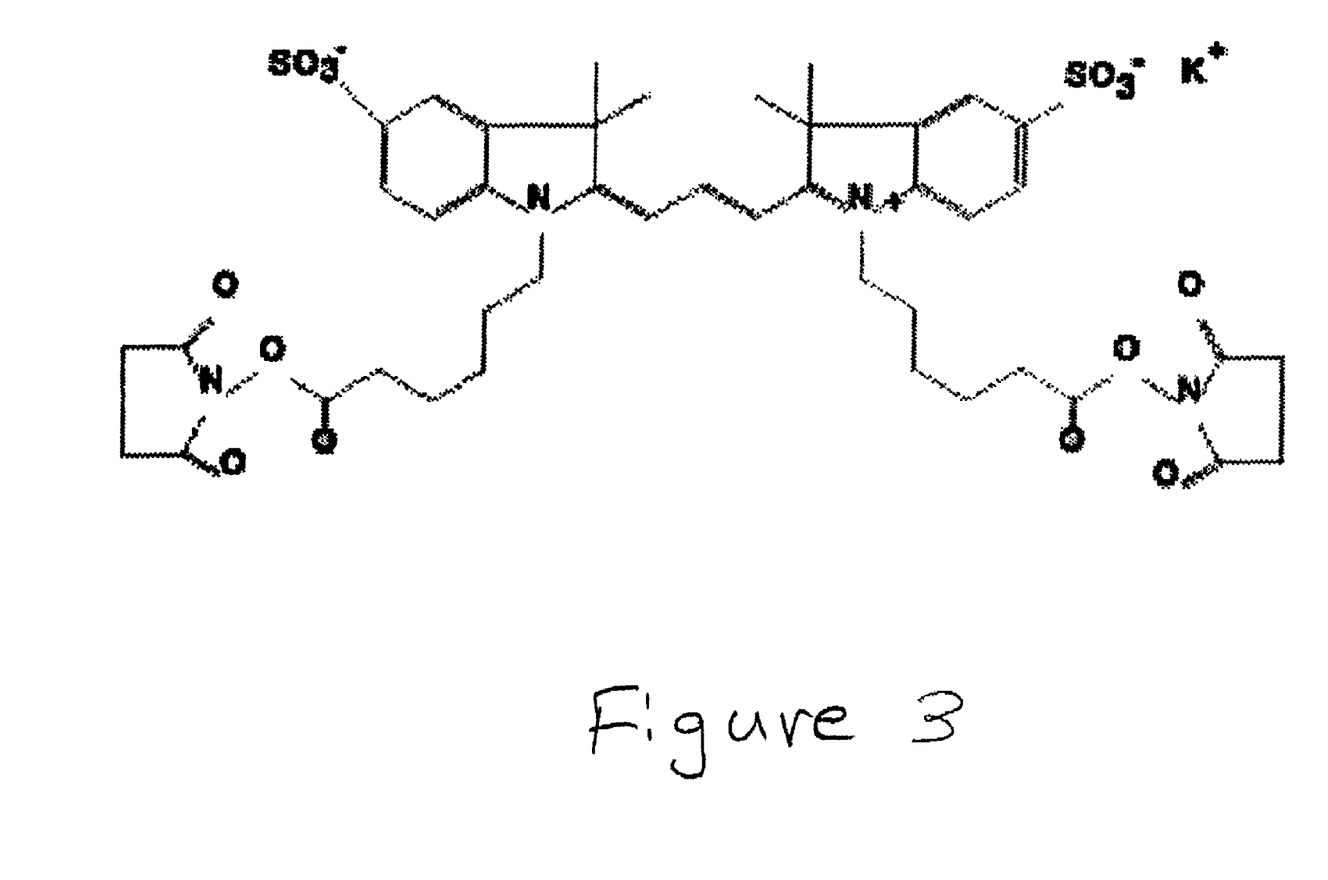
FIG. 3 shows the chemical structure of Cy3™.

If a dye, such as, FAM, is used as the fluorophore, then detection of the reporting DNA sequence by flow cytometry will not be possible using a Luminex™ 100 analyzer because FAM does not emit at a wavelength seen by the flow cytometer. Two methods are disclosed which overcome this problem. The first method replaces a rhodamine reporter dye, such as, FAM, at the 5' end with a water-soluble cyanine dye, such as, Cy3™, the structure of which is shown in FIG. 3. Both the real time PCR instruments and flow cytometers can detect Cy3™. A Cy3™ quencher such as, Black Hole Quencher-2 (BHQ™-2) from Biosearch Technologies, Inc. replaces the rhodamine quencher dye, such as, TAMRA, at the 3' end of the reporting DNA sequence. A change in the fluorescence of any reporting DNA sequence indicates the existence of the target DNA sequence specified by the reporting DNA sequence. Multiplex PCR amplification and subsequent hybridization and detection by flow cytometery are possible using a reporting DNA sequence with only a reporter dye, such as, Cy3™, linked to the 5'end and no quencher dye linked to the 3' end. However, if no quencher is linked to the 3' end, then there can be no real time PCR detection coupled to the flow cytometry.

The second method that allows real time PCR detection to be coupled with flow cytometry uses a modified reporting DNA sequence that reverses the location of reporter and quencher dyes. The method positions the reporter dye, e.g., FAM, on the 3' end and the quencher dye, e.g., TAMRA, on the 5' end. Other examples of reporter/quencher pairs include Cy3™/BHQ™-2 and Cy5™/BHQ™-3. This method is effective for two reasons: (1) the quencher dye is detectable by flow cytometry and (2) real time PCR detection is not adversely effected by changing the location of the dyes because once the reporting DNA sequence is cleaved, the reporter dye will be detected as long as the quencher dye is no longer in close proximity to it. Detection occurs whether the reporter dye melts off or remains linked to the reporting DNA sequence.

The microsphere-based hybridization reaction can be effectively performed with either Avidin coated or Carboxylated microspheres. Polystyrene microspheres manufactured by Luminex Corporation ordered as Lum-Avidin™ Microspheres are effective, but microspheres made of different materials and/or manufactured by other vendors can also be used. Multiplex analysis is possible because the microspheres are optically encoded with two fluorescent dyes in varying concentrations, thereby creating a population of microspheres, i.e., a set of microspheres, distinguishable by the amount of dyes present within them. Each set of microspheres can be linked to a different oligonucleotide probe that is complementary to a specific target sequence, i.e., the complement of the reporting DNA sequence, used in the PCR reaction. Currently this method allows for the simultaneous detection of about 100 different signatures. Detection can be accomplished by using a flow cytometer, e.g., a Luminex 100™ analyzer, or other flow cytometry means. Flow cytometry determines whether a reduction in fluorescence occurred which would be indicative of a positive reaction. In contrast, if no reaction occurred, no change in fluorescence will be detected.

As discussed above, the reporter-quencher pair normally used in a Taqman® assay can be modified by locating the quencher at the 5' end of the reporting DNA sequence and locating the fluorophore, also called the reporter, at the 3' end to form a reporting DNA sequence that can be described as a "reverse-Taqman® probe". During this modified-Taqman® amplification reaction, the enzyme will cleave the quencher from the reporting DNA sequence if the target sequence is present. The PCR amplified product containing the reporting DNA sequence fragment linked to the quencher is added to oligonucleotide probes bound to microspheres, wherein the probes are complementary to the reporting DNA sequences. For example, avidin microspheres ordered from Luminex as Lum-Avidin™ Microspheres can be conjugated to Biotin Labeled Probes complementary to the reporting DNA sequences using the protocol obtained from Luminex Corporation. The protocol can be found at the web address luminexcorp.com. An effective microsphere mix contains $10^2$ microspheres per µL in a PCR buffer solution, e.g., 2.5M TMAC, 0–15% SDS, 3 mM EDTA, 75 mM Tris-HCl, pH of 8. Hybridization can be accomplished by combining about 10 µL of the microsphere mix with about 25 µL of the PCR reaction product and mixing at room temperature for about 15 minutes. This method differs from conventional hybridization in that it requires no temperature control since the hybridization products, e.g., the undigested reporting DNA sequences, are already present as single strands in the PCR mix.

EXAMPLES

Example 1

About a 25 µL mixture of about 2.5 µL of 1×PCR buffer, about 6 mM of Sigma® 1 Molar solution of $MgCl_2$ (Sigma® solution number M1787), about 2.5 mM of each dNTPS (Roche pharmaceuticals catalog # 1051440 dATP, #1051458 dCTP, #1420470 dUTP, #1051466 d GTP), 1.25 U of Pt Taq polymerase (Life Technologies-Gibco BRL catalog # 10955-034), 400 nM of each primer and each reporting DNA sequence labeled with Cy3™ on the 5' end and no quencher on the 3'end (dilution of the reporting DNA sequence is dependant on the signal intensity, the amount typically used is in the range 35 nM to 100 nM determined by a simple titration experiment), about 5 µL of sample and the balance PCR water (Sigma® W4502). An initial single cycle of 96° C. for 1 minute was used followed by 40 cycles of the PCR thermal cycling parameters for *Erwinia herbicola* (Eh), i.e., 94° C. for 15 seconds: 57° C. for 15 seconds using an ABI 7700.

Figure 4:
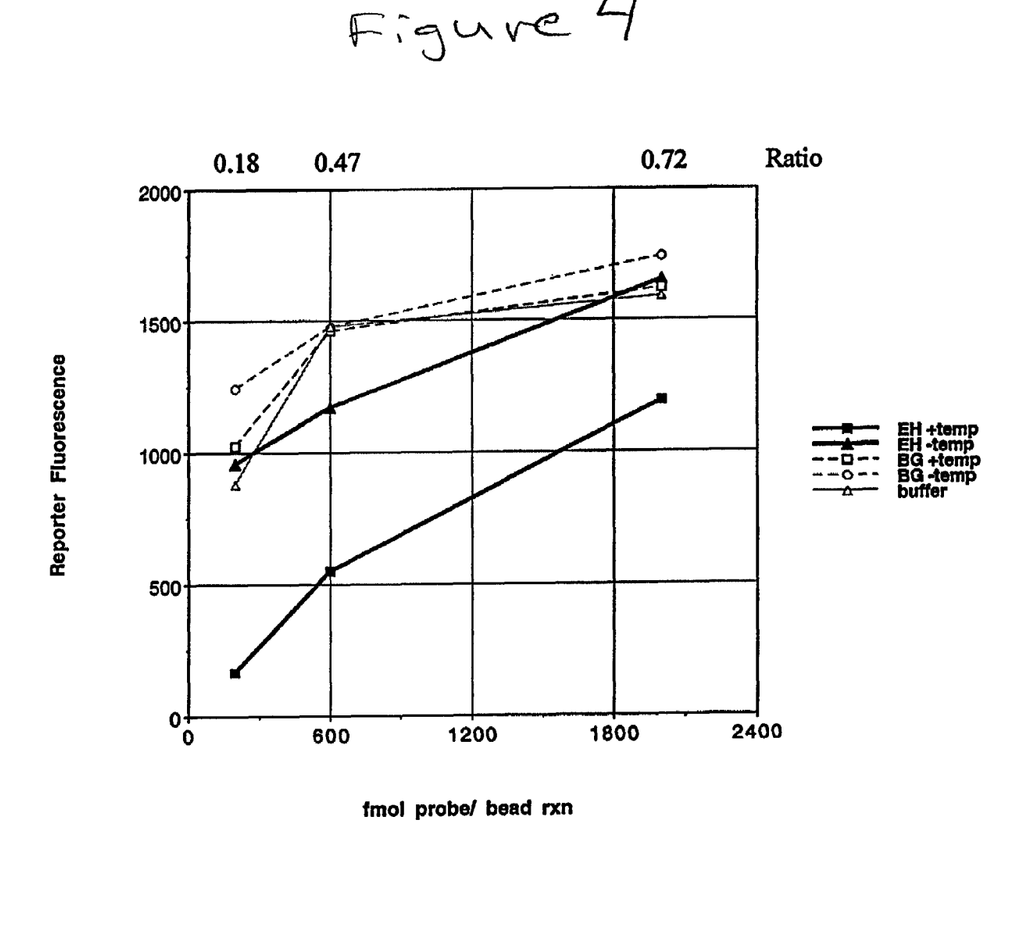
FIG. 4 shows flow cytometry results using Cy3™ labeled DNA reporting sequence.

A microsphere mix was prepared comprising $10^2$ microspheres per µL in a PCR buffer solution, e.g., 2.5M TMAC, 0–15% SDS, 3 mM EDTA, 75 mM Tris-HCl, pH of 8. Hybridization was accomplished by combining about 10 µL of the microsphere mix with about 25 µL of the PCR reaction product and mixing at room temperature for about 15 minutes. The hybridization products were then analyzed using a Luminex 100™ analyzer. Referring to FIG. 4,

*Erwinia herbicola* (Eh) specific sequences were detected by a Cy3™ fluorescent reporter labeled reporting DNA sequence.

Example 2

About a 25 µL mixture of about 2.5 µL of 1×PCR buffer, about 6 mM of Sigma® 1 Molar solution of MgCl$_2$ (Sigma® solution number M1787), about 2.5 mM of each dNTPS (Roche pharmaceuticals catalog # 1051440 dATP, #1051458 dCTP, #1420470 dUTP, #1051466 d GTP), 1.25 U of Pt Taq polymerase (Life Technologies-Gibco BRL catalog # 10955-034), 400 nM of each primer and 80 nM of each reporting DNA sequence, about 5 µL of sample containing Eh and Bg and the balance PCR water (Sigma® W4502). The reporting DNA sequence concentrations have to be more dilute than in conventional assays to keep the signal in the linear range. If the reporting DNA sequence is too concentrated in the reaction then one will not see a clear positive. An initial single cycle of 96° C. for 1 minute was used followed by 40 cycles of the PCR thermal cycling parameters for *Erwinia herbicola* (Eh), i.e., 94° C. for 15 seconds: 57° C. for 15 seconds, using an ABI 7700.

Figure 5:
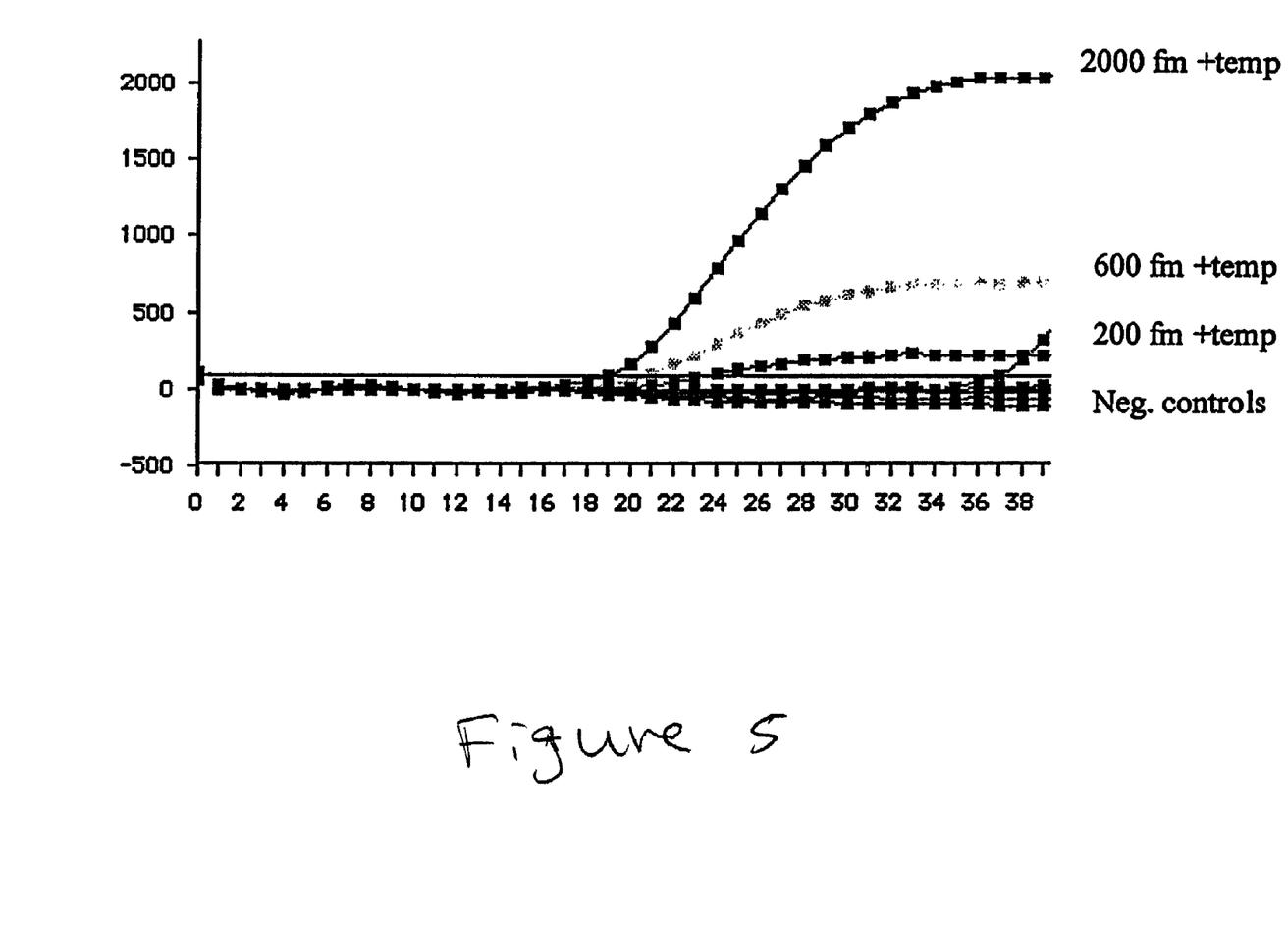
FIG. 5 shows flow cytometry results using a TAM-FAM labeled DNA reporting sequence.

A microsphere mix was prepared containing about $10^2$ microspheres per µL in a PCR buffer solution of 2.5M TMAC, 0–15% SDS, 3 mM EDTA, 75 mM Tris-HCl, pH of 8. Hybridization was accomplished by combining about 10 µL of the microsphere mix with about 25 µL of the PCR reaction product and mixing at room temperature for about 15 minutes. The hybridization products were then analyzed using a Luminex 100™ analyzer. FIG. 5 demonstrates how the assay specifically detected only the Eh amplification and not the unrelated *Bacillus globigii* amplification.

While a particular embodiment of the invention has been illustrated and described, along with a listing of potential embodiments therefor and particular parameters, to exemplify and teach the principles of the invention, such are not intended to be limiting. Modifications and changes may become apparent to those skilled in the art, and it is intended that the invention be limited only by the scope of the appended claims.

We claim:

1. A method for multiplexed detection of PCR amplified products comprising:

providing a DNA sample having up to about one-hundred unique target DNA sequences of interest for a sample multiplex PCR amplification reaction, providing necessary reagents and primers for said sample multiplex POR amplification reaction, forming a sample PCR product by conducting said sample multiplex PCR amplification reaction using said DNA sample having up to about one-hundred unique target DNA sequences of interest, a unique reporting DNA sequence complementary to a region on each target DNA sequence, wherein each reporting DNA sequence includes a fluorescence resonant energy transfer marker means, forming a microsphere mix comprising a plurality of optically encoded microspheres, each microsphere having a unique physically-detectable code, each microsphere bound to a unique biotinylated oligonucleotide, wherein each unique physically-detectable code corresponds to specific oligonucleotide having a DNA sequence complementary to each unique reporting DNA sequence, forming a sample hybridization product by adding said sample PCR product to said microsphere mix, forming a background PCR product by conducting a background multiplex PCR amplification reaction using at least one control DNA sequence, the control DNA sequence differing from each of the target DNA sequences of interest, wherein said background PCR amplification reaction is run under the same conditions and using the same primers and reagents as said sample PCR amplification reaction, forming a background hybridization product by adding said background PCR product to said microsphere mix, wherein the presence or absence of false positives is determined; and determining the existence of each of said target DNA sequence of interest specified by said reporting DNA sequence by comparing the fluorescence of said sample hybridization product with said background hybridization product using flow cytometry.

2. The method recited in claim 1, wherein the hybridization reaction is performed with no temperature controls.

3. The method recited in claim 1, wherein the microspheres are avidin coated.

4. The method recited in claim 1, wherein the microspheres are polystyrene.

5. The method recited in claim 1, wherein the existence of said target DNA sequence specified by said reporting DNA sequence is indicated by a decrease in fluorescence observed in said sample hybridization product compared to said background hybridization product during flow cytometry.

6. The method recited in claim 1, wherein the fluorescence resonant energy transfer marker means comprises a fluorophore and quencher wherein excision of the quencher activates the fluorophore.

7. The method recited in claim 6, wherein the fluorophore is attached to a 5' end of the reporting sequence, and the quencher is attached to a 3' end of the reporting sequence.

8. The method recited in claim 6, wherein the fluorophore is attached to a 3' end of the reporting sequence, and the quencher is attached to a 5' end of the reporting sequence.

9. The method recited in claim 1, wherein the fluorescence resonant energy transfer marker means is the same for each reporting DNA sequence.

10. The method recited in claim 1, wherein said up to about one hundred DNA sequences of interest are simultaneously detected.

11. The method recited in claim 1, wherein the unique detectable code is optically-detected, based upon varying concentrations of at least two dyes.

12. The method recited in claim 1, wherein the method of multiplexed detection of PCR amplified products occurs within about forty minutes.

13. The method recited in claim 1, wherein the fluorescent energy transfer means comprises 1-(epsilon-carboxypentyl)-1'-ethyl-3,3,3',3'-tetramethylindocarbocyanine-5,5'-disulfonate potassium salt N-hyroxysuccinimide ester as a fluorphore.

14. A method for multiplexed detection of PCR amplified products comprising:

providing a DNA sample having up to about one-hundred unique target DNA sequences of interest for a sample multiplex PCR amplification reaction, providing necessary reagents and primers for said sample multiplex PCR amplification reaction, forming a sample PCR product by conducting said sample multiplex PCR amplification reaction using said DNA sample having up to about one-hundred unique target DNA sequences of interest, a unique reporting DNA sequence complementary to a region on each target DNA sequence, wherein the reporting DNA sequence includes a fluorescent resonant energy transfer marker means comprising a fluorophore quencher pair in operative relationship to one another, providing necessary reagents and primers for a background multiplex PCR amplification reaction and forming a background PCR product by conducting said background multiplex PCR amplification reaction using at least one control DNA sequence, wherein said background PCR amplification reaction is run under the same conditions and using the same primers, reagents and reporting DNA sequences as said sample PCR amplification reaction, determining with fluorescence detecting means whether a difference in fluorescence exists between said sample PCR product and said background PCR product, said difference being indicative of the multiplex PCR amplification reaction resulting in the formation of (1) at least one PCR amplification product and (2) at least one residual reporting sequence containing said quencher, forming a microsphere mix comprising a plurality of unique optically encoded microspheres, each microsphere bound to a unique oligonucleotide, wherein each optical code corresponds to specific oligonucleotide having a DNA sequence complementary to each unique reporting DNA sequence, forming a sample hybridization product by adding said sample PCR product to said microsphere mix, forming a background hybridization product by adding said background PCR product to said microsphere mix wherein the presence or absence of a false positive is determined, determining the existence of each of said target DNA sequence of interest specified by said reporting DNA sequence by comparing the fluorescence of said sample hybridization product with said background hybridization product using flow cytonietry.

15. The method recited in claim 14, wherein the oligonueleotides are biotinylated.

16. The method recited in claim 14, wherein the hybridization reaction is performed with no temperature controls.

17. The method recited in claim 14, wherein the microspheres are avidin coated.

18. The method recited in claim 14, wherein the mierospheres are polystyrene.

19. The method recited in claim 14, wherein the existence of said target DNA sequence specified by said reporting DNA sequence is indicated by a decrease in fluorescence observed in said sample hybridization product compared to said background hybridization product during flow cytometry.

20. The method recited in claim 14, wherein an increase in fluorescence observed in said sample PCR product compared to said background PCR product using fluorescence detecting means indicates the existence of at least one target DNA sequence specified by said reporting DNA sequence.

21. A method for multiplexed detection of PCR amplified products comprising:

providing a DNA sample having up to about one-hundred unique target DNA sequences of interest for a sample multiplex PCR amplification reaction, providing necessary reagents and primers for said sample multiplex PCR amplification reaction and a background multiplex PCR amplification reaction, forming a sample PCR product by conducting said sample multiplex PCR amplification reaction using said DNA sample, at least one reporting DNA sequence complementary to a region on at least one target DNA sequence of interest wherein the reporting DNA sequence includes a fluorescence resonant energy transfer means, comprising a quencher on the 5' end and a fluorophore on the 3' end, forming a background PCR product by conducting said background multiplex PCR amplification reaction, wherein said background PCR amplification reaction is run under the same conditions and using the same printers, reagents and reporting DNA sequences as said sample PCR amplification reaction, determining with fluorescence detecting means whether a difference in fluorescence exists between said sample PCR product and said background PCR product, said difference being indicative of the multiplex PCR amplification reaction resulting in the formation of (1) at least one PCR amplification product and (2) at least one residual reporting sequence containing said fluorophore, forming a microsphere mix comprising a plurality of optically encoded microspheres bound to a plurality of biotinylated oligonucleotides, wherein each optical code corresponds to specific oligonucleotide having a DNA sequence complementary to at least one reporting DNA sequence of interest, forming a sample hybridization product by adding said sample PCR product to said microsphere mix, forming a background hybridization product by adding said background PCR product to said microsphere mix, wherein the presence or absence of a false positive is determined; and determining the existence of said target DNA sequence specified by said reporting DNA sequence by comparing the fluorescence of said sample hybridization product with said background hybridization product using flow cytometry.

22. The method recited in claim 21, wherein the hybridization reaction is performed with no temperature controls.

23. The method recited in claim 21, wherein the microspheres are avidin coated.

24. The method recited in claim 21, wherein the microspheres are polystyrene.

25. The method recited in claim 21, wherein the quencher on the 5' end is TAMRA.

26. The method recited in claim 21, wherein the fluorophore on the 3' end is FAM.

27. The method recited in claim 21, wherein the existence of said target DNA sequence specified by said reporting DNA sequence is indicated by a decrease in fluorescence observed in said sample hybridization product compared to said background hybridization product during flow cytotnetry.

28. The method recited in claim 21, wherein an increase in fluorescence observed in said sample PCR product compared to said background PCR product using fluorescence detecting means indicates the existence of at least one target DNA sequence specified by said reporting DNA sequence.

29. The method recited in claim 21, wherein the fluorophore comprises 1-(epsilon-carboxypentyl)-1'-ethyl-3,3,3',3'-tetramethylindocarbocyanine-5,5'-disulfonate potassium salt N-hyroxysuccinimide ester as a fluorophore.

30. The method recited in claim 21, wherein the detection of the target DNA sequence of interest occurs within about 40 minutes.

* * * * *